US012653983B2

(12) United States Patent
Adriaenssen et al.

(10) Patent No.: US 12,653,983 B2
(45) Date of Patent: Jun. 16, 2026

(54) RESPIRATION GUIDANCE DEVICE

(71) Applicant: MOONBIRD BV, Keerbergen (BE)

(72) Inventors: Ward Adriaenssen, Schoten (BE); Tim Ruytjens, Mortsel (BE); Martijn Vanschoenwinkel, Mechelen (BE); Michael Broes, Keerbergen (BE)

(73) Assignee: MOONBIRD BV, Keerbergen (BE)

( * ) Notice: Subject to any disclaimer, the term of this patent is extended or adjusted under 35 U.S.C. 154(b) by 968 days.

(21) Appl. No.: 17/801,707

(22) PCT Filed: Feb. 23, 2021

(86) PCT No.: PCT/EP2021/054467
§ 371 (c)(1),
(2) Date: Aug. 23, 2022

(87) PCT Pub. No.: WO2021/170589
PCT Pub. Date: Sep. 2, 2021

(65) Prior Publication Data
US 2023/0166071 A1 Jun. 1, 2023

(30) Foreign Application Priority Data

Feb. 24, 2020 (EP) .................................... 20159156

(51) Int. Cl.
*A61M 21/02* (2006.01)
*A61M 21/00* (2006.01)

(52) U.S. Cl.
CPC ..... *A61M 21/02* (2013.01); *A61M 2021/0022* (2013.01); *A61M 2021/0088* (2013.01); *A61M 2230/06* (2013.01)

(58) Field of Classification Search
CPC .......... A61M 21/02; A61M 2021/0022; A61M 2021/0088; A61M 2230/06;
(Continued)

(56) References Cited

U.S. PATENT DOCUMENTS 4,606,328 A * 8/1986 Thoman ................. A63H 3/001
446/295
10,201,236 B1 * 2/2019 Cloud .................. A47G 9/1045
(Continued)

FOREIGN PATENT DOCUMENTS

DE 102008030956 A1 4/2009
EP 2311533 A1 4/2011

OTHER PUBLICATIONS

Search Report from corresponding European Application No. EP 20159156.7, Aug. 21, 2020.
(Continued)

*Primary Examiner* — Sunita Reddy
(74) *Attorney, Agent, or Firm* — Workman Nydegger

(57) ABSTRACT

Various example embodiments relate to a respiration guidance device including: an outer casing configured to change shape; and a drive unit located within the outer casing and configured to change the shape of the outer casing according to a desired breathing pattern; and the outer casing has at least one slit dividing the outer casing into at least one portion displaceable with respect to a remaining portion of the outer casing; and the drive unit is configured to change the shape of the outer casing by displacing the at least one portion.

10 Claims, 7 Drawing Sheets

(58) Field of Classification Search
CPC ........ A61B 5/02438; A61B 2560/0425; A61B
5/6898; A61B 5/7455; A61B 5/486; A63B
2071/0655; A63B 2230/062; A63B
2230/305; A63B 2230/425; A63B 23/185
USPC ..................................................... 600/26–28
See application file for complete search history.

(56) References Cited

U.S. PATENT DOCUMENTS

| | | | |
|---|---|---|---|
| 10,258,259 B1 | 4/2019 | Zets et al. | |
| 2013/0190554 A1* | 7/2013 | Vogt ..................... | A63B 23/185 |
| | | | 600/27 |
| 2013/0231522 A1* | 9/2013 | Krans ................. | A61B 5/0816 |
| | | | 600/26 |
| 2013/0310636 A1* | 11/2013 | Krans ................... | A61B 5/486 |
| | | | 600/26 |
| 2017/0202507 A1 | 7/2017 | Plans Casal et al. | |
| 2018/0056029 A1* | 3/2018 | Akimoto ................... | G04F 5/02 |
| 2022/0047841 A1* | 2/2022 | Durán Vargas ...... | A61H 9/0092 |

OTHER PUBLICATIONS

International Search Report from PCT Application No. PCT/EP2021/054467, May 6, 2021.

* cited by examiner

RESPIRATION GUIDANCE DEVICE

TECHNICAL FIELD

Various example embodiments relate to the field of pacing the respiratory activity of a user, and, more specifically to respiration guidance devices.

BACKGROUND

Regular and slow breathing activity is considered to be beneficial for relaxation and stress reduction. Regular slow breathing activity is practiced during yoga and meditation. Further regular slow breathing activity is used as stress and blood pressure control. Respiration guidance devices using sound, optical and/or tactile or haptic signals to assist users in regulating and/or slowing down their breathing to a pre-determined breathing pattern are known in the art.

A tactile or haptic signal may be provided by a tactile unit that changes shape or size periodically or which vibrates with periodically varied intensity. Respiration guidance devices providing tactile signals by changing the shape of the tactile unit are however rather complex, bulky and therefore costly. Further, such devices cannot be used discreetly by the users at any time when needed.

U.S. Pat. No. 10,258,259 B1 relates to a system and method for measuring the biomechanical state of a subject using various sensors simultaneously with providing the subject with visual exercises for rehabilitation and assessment of disequilibrium, balance and motion disorders.

EP 2311533 A1 relates to a respiration controlling apparatus for controlling the respiration of a person. The respiration controlling apparatus generates a heart rate signal indicative of the heart rate of the person, determines a desired breathing sequence based on the generated hear rate signal and outputs a haptic output signal depending on the determined desired breathing sequence.

SUMMARY

Amongst others, it is an object of embodiments of the present disclosure to provide a compact and less costly respiration guidance device which provides a reliable and an intuitive tactile signal. A further object of embodiments of the present disclosure is to provide a respiration guidance device which offers a long lifetime and which may be used discreetly at any time.

The scope of protection sought for various embodiments of the invention is set out by the independent claims.

The embodiments and features described in this specification that do not fall within the scope of the independent claims, if any, are to be interpreted as examples useful for understanding various embodiments of the invention.

This object is achieved, according to a first example aspect of the present disclosure, by a respiration guidance device, comprising:

an outer casing configured to change shape; and a drive unit located within the outer casing and configured to change the shape of the outer casing according to a desired breathing pattern; and wherein the outer casing comprises at least one slit dividing the outer casing into at least one portion displaceable with respect to a remaining portion of the outer casing; and wherein the drive unit is configured to change the shape of the outer casing by displacing the at least one portion.

By providing one or more slits in the outer casing, one or more displaceable portions with respect to the remaining portion are obtained. The displacing causes the outer casing to change its shape and dimensions. The outer casing thus acts as a tactile unit and thus provides a tactile signal. Such a tactile signal is an intuitive and easily perceivable tactile signal. The dimensions of the at least one displaceable portion define the tactile area, i.e. the area which changes shape and dimensions. The respiration guidance device may be made compact as no complex and bulky mechanism to modify the shape of the device is required. The device may be made so compact so it can be discreetly held in hand. Furthermore, this allows the outer casing to be made of non-flexible rigid materials as change of shape is provided by the flexible portions. Additionally, the use of non-flexible rigid materials for the outer casing allows protecting the drive unit from damages.

By changing the shape and dimensions of the slits, the shape and dimensions of the displaceable portions and therefore the tactile area may be easily defined.

Further, by controlling the drive unit in accordance with the desired breathing pattern, the change of shape and therefore the tactile signal, may be easily controlled to provide various tactile signals to assist users in regulating, slowing down or pacing up their breathing to a desired breathing pattern.

According to example embodiments, the at least one portion comprises at least one flexible portion configured to connect the at least one portion with the remaining portion.

The flexible portion forms a "hinge" area or a hinge mechanism which connects the displaceable portions with the remaining portion of the outer casing. The hinge is a flexible hinge made from the same material as the outer casing. Such a hinge allows the displaceable portions to be displaced, for example, to bend (or flex) along the line of the hinge. Such a hinge mechanism is similar to a living hinge with the difference that there is no thinning or a cut along the line of the hinge. It offers minimal friction and little wear in the hinge and, therefore, a long lifetime. As a result, a reliable, low cost and easy to manufacture outer casing acting as a tactile unit may be obtained.

According to example embodiments, the outer casing is configured to expand or contract upon displacing the at least one portion with respect to the remaining portion.

Expanding of the outer casing may be easily achieved by displacing, for example, by pushing the displaceable portion outwards with respect to the outer casing. Alternatively, the outer casing may contract, by pulling the displaceable portions inwards with respect to the outer casing.

The expanding or contracting causes the outer casing to change its shape and dimensions and thus to output a tactile signal which assist users in regulating and/or slowing down their breathing.

According to example embodiments, the outer casing comprises a first section and a second section configured to be fastened together, each section comprising at least one slit dividing the respective section into at least one portion displaceable with respect to a remaining portion of the respective section, and, wherein the drive unit is configured to change the shape of the respective sections by displacing their respective at least one portion.

By configuring both sections to change shape, the tactile area may be increased. This way, a respiration guidance device with an increased tactile area may be manufactured. Further, the first and second sections may be designed to have the same or similar tactile area. Therefore, both sections will change their shape in the same or similar way. A symmetrical design may thus be achieved which allows convenient use and a good tactile perception of different users. Further, design of the cantilever and/or the displaceable portions may be reused. This simplifies the manufacturing process and lowers the manufacturing costs.

Further, depending on the design of the displaceable portions, a substantial part of the surface or the entire surface of the outer casing may change shape.

According to example embodiments, the first section and the second section are configured to expand or contract simultaneously upon displacing the respective at least one portions.

By simultaneously expansion or contraction of both sections, the range of expansion is doubled. Further, the range of expansion of one of the sections may be designed to be more extensive than the other. This way, a respiration guidance device for a specific user group, for example, a right-hand or a left-hand user, may be provided. Further, simultaneous expansion or contraction of both sections allows the device to be held with both hands.

According to other example embodiments, the drive unit comprises a camshaft for translating a rotational movement into the displacement of the outer casing.

The camshaft comprises a cam, a rotating piece, which transforms the rotary motion of the shaft into a linear motion. The cam thus produces a reciprocating linear motion, for example, an up and down or a back and forth motion, in an object engaged with the cam. This object is typically referred to as a follower and is placed so that it is in contact with rim, i.e. the outer edge, of the cam. As the cam rotates, the cam pushes the follower up and down or back and forth. The cam may have different shapes and dimensions, for example, an elliptical wheel or an eccentric wheel with a circular shape or any other shape suitable to provide the required tactile output. In case the cam is an elliptical wheel, different and/or complex tactile outputs may be obtained by controlling how the drive unit rotates the camshaft. For example, the drive unit may be arranged to rotate slower for a fourth of the rotation cycle and faster for the another fourth of the rotation cycle. This way, a breathing pattern with a slower 'breathe in' phase and a faster 'breathe out' phase may be emulated. A 'breathe hold' phase between 'breathe in' and 'breathe out' phases may be emulated by slowing down the rotation of the drive unit to a complete stop. Such an implementation requires a more sophisticated control of the drive unit. Alternatively, the cam may have a complex shape suitable to provide such complex tactile outputs. In this case, the control complexity of the drive unit is partially or entirely migrated to the design of the cam. In the case when the control complexity is entirely migrated to the cam, the drive unit will rotate at a constant pace while the shape of the cam will define the breathing pattern.

According to example embodiments, the drive unit further comprises at least one cantilever for transforming the movement of the camshaft into the displacement of the outer casing.

One or more cantilevers may be used as a follower which displace the displaceable portion of the outer casing. For example, the displaceable portion may be moved up and down which in turn results in emulating a breathing pattern by expanding and contracting the outer casing.

By appropriately designing the cantilever, the cam may be made compact. This reduces the load on the motor as the motor needs to drive (rotate) a smaller cam. Further, bigger range of displacement may be achieved, while maintaining the same or similar load on the motor.

According to example embodiments, the at least one cantilever is configured to engage with the at least one portion at one end and to engage with the camshaft at the other end.

This way, by using a cantilever as a follower, the drive unit may create the same breathing pattern by using less power to drive (or rotate) the camshaft. Therefore, the drive unit may be less powerful and hence more compact.

According to example embodiments, the at least one cantilever is configured to engage with the at least one portion at multiple locations.

By configuring the cantilever to engage with the displaceable portion at multiple locations, a good contact is guaranteed between the cantilever and the displaceable portion. This lowers the design complexity of the cantilever. For example, cantilever end which engages with the displaceable portion may be designed to have an elongated shape. Further, the latter may be designed to have a curved shaped. This allows improving the gradual expansion and contraction throughout the tactile area of the outer casing.

According to example embodiments, the at least one cantilever is configured to disengage upon exerting external pressure on the outer casing.

Advantageously, in case of applying excessive pressure onto the device, e.g. by excessively squeezing the device, the cantilever will disengage from the cam and therefore will not be in contact with the cam. This allows the camshaft to continue rotating freely without exerting an excessive force to the drive unit. Damage of the drive unit is thus prevented.

According to further example embodiments, the respiration guidance device further comprises at least one sensor configured to generate an electrical signal indicative of a physiological characteristic of a person, and, a control unit configured to determine the desired breathing pattern based on the generated electrical signal and to operate the drive unit in accordance with according to the desired breathing pattern.

A physiological characteristic of the user may be, for example, the user's heart rate, blood pressure, breathing rate or stress level. These physiological characteristics provide an indication of the breathing pace of the user. Thus, by determining the desired breathing pattern based on the generated electrical signal, the current physiological characteristic of the user may be considered when determining the desired breathing pattern. This way, if the heart rate of the user is elevated, for example due to stress, the breathing of the user may be guided from a stress state to a desired relax state. Alternatively, the breathing of the user may be guided to a more energized state, for example during meditation. The user's breathing may thus be paced down or up gradually until the desired breathing pattern is reached.

According to example embodiments, the at least one sensor comprises a heart rate sensor for generating an electrical signal indicative of a heart rate of the person.

A heart sensor may be used to provide indication of the physiological characteristics of the user. The heart sensor may be an electrocardiography, ECG, sensor or a photoplethysmography, PPG, sensor. Sensors detecting electrodermal activity, EDA, may also be used alone or in combination with a heart sensor. EDA sensors provide information of the emotional state of the user, e.g. stress, happiness.

According to example embodiments, the outer casing may be covered by or enclosed within a flexible material.

By covering the outer casing with a flexible material, the gradual (or smooth gradation of the) expansion and contraction throughout the tactile area of the outer casing may be further improved. The flexible material may be a sleeve placed on top of the outer casing. The sleeve may be made of silicon, a foam or an elastic textile material. The elastic textile material may be for example made of elastic synthetic fibres, such as spandex or elastane. Further, the device becomes airtight and is therefore protected from dust and dirt. Further, the flexible material may act as a shock absorbent and may thus prevent the respiration guidance device from damages. Even more, the respiration guidance device has a smoother and more comfortable and pleasant to touch feel.

According to example embodiments, the flexible material may comprise the skin-based heart rate sensor, such as an ECG sensor.

An ECG sensor may be embedded or interwoven in the flexible material. This way, part of or the whole textile material may serve as an ECG sensor. The sensing surface of the ECG sensor is thus increased.

By enclosing the outer casing within the flexible material, the flexible material may act as a flexible portion between the displaceable portion and the remaining portion of the outer casing. A hinge mechanism or flexure bearings may not be required. Therefore, the design requirements of the displaceable portion and the cantilever are more relaxed.

The respiration guidance device according to any of the preceding claim, wherein the device is a hand-held.

By designing the respiration guidance device to be a hand-held, the device may be discreetly held in hand or with both hands. The device, thus, may be conveniently used at any time and at any place.

BRIEF DESCRIPTION OF THE DRAWINGS

Some example embodiments will now be described with reference to the accompanying drawings.

DETAILED DESCRIPTION OF
EMBODIMENT(S)

Figure 1A:
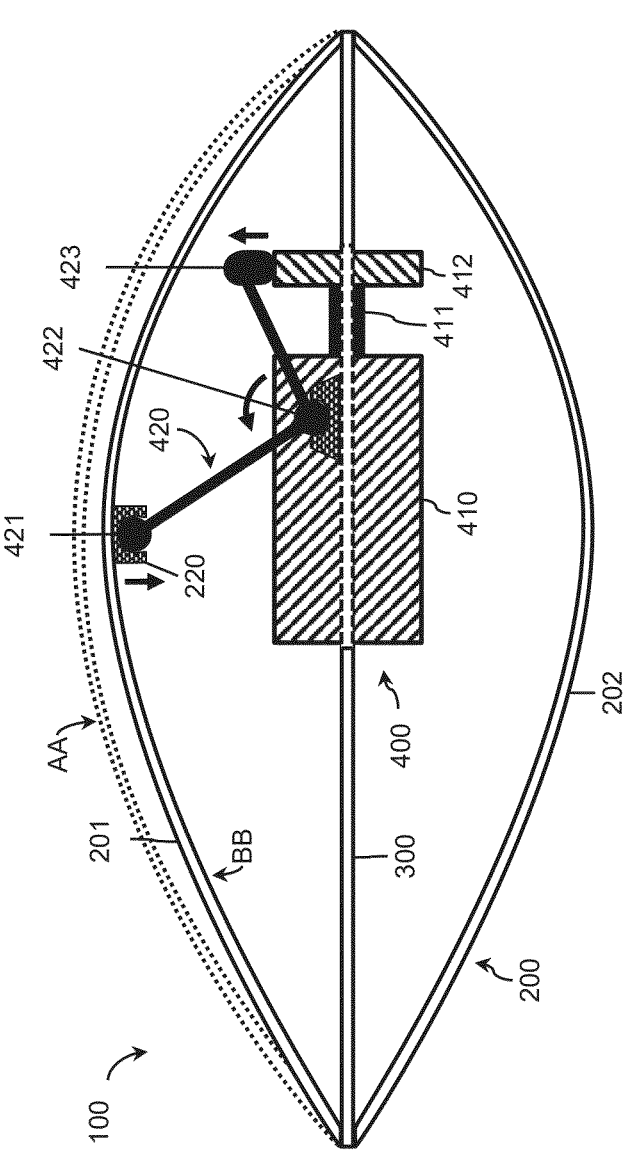
FIG. 1A shows an example embodiment of the respiration guidance device according to the present disclosure.

FIG. 1A shows a first example embodiment of a respiration guidance device 100 according to the present disclosure. The device 100 comprises an outer casing 200 and a drive unit 400 mounted on a platform 300 located within the outer casing 200. The platform 300 may be located in the middle of the outer casing as shown in the figure. The platform is made of a non-flexible rigid material, such as plastic or aluminium, to hold firmly the drive unit in place.

The outer casing 200 may also be made of such non-flexible rigid materials. Alternatively, the outer casing may be made of a semi-rigid material such as plastic, silicone, Polyurethane, thermoplastic elastomers, TPE, or similar. The outer casing may be produced by three-dimensional, 3D, printing, or, by using an injection moulding or a computer numerical control, CNC, machining techniques. The outer casing may be covered with or enclosed within a flexible material, such as a silicon skin (not shown in the figure). The flexible material may as well be made of textile material, gel-like material, or, a foam, such as thermoplastic polyurethane, TPU, foam or other.

The outer casing 200 may be composed of two or more sections 201 and 202 which when fasten together form the outer casing. The sections 201 and 202 may be glued or screwed together. For example, the section 201 may be provided with holes 211 and 212 for the screws to be inserted and the bottom section 202 may be provided with internal threaded areas to receive the screws. When the sections 201 and 202 are made of aluminium, it is preferred that they are screwed together. If they are made of plastic, they may be either glued or screwed together.

Figures 2A, 2B, 2C:
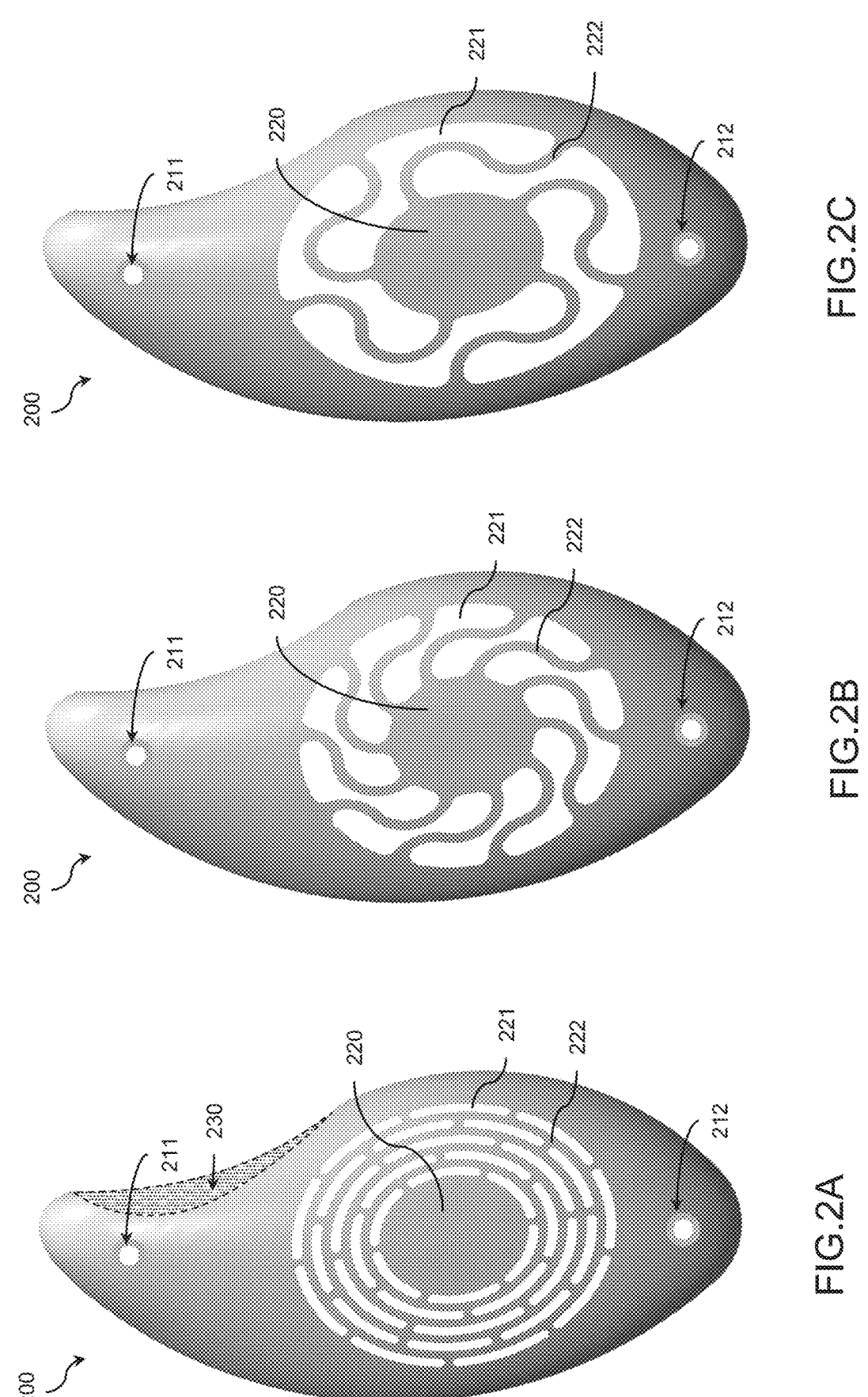
FIG. 2A to FIG. 2H shows various example embodiments of the outer casing according to the present disclosure.
Figures 2D, 2E, 2F:
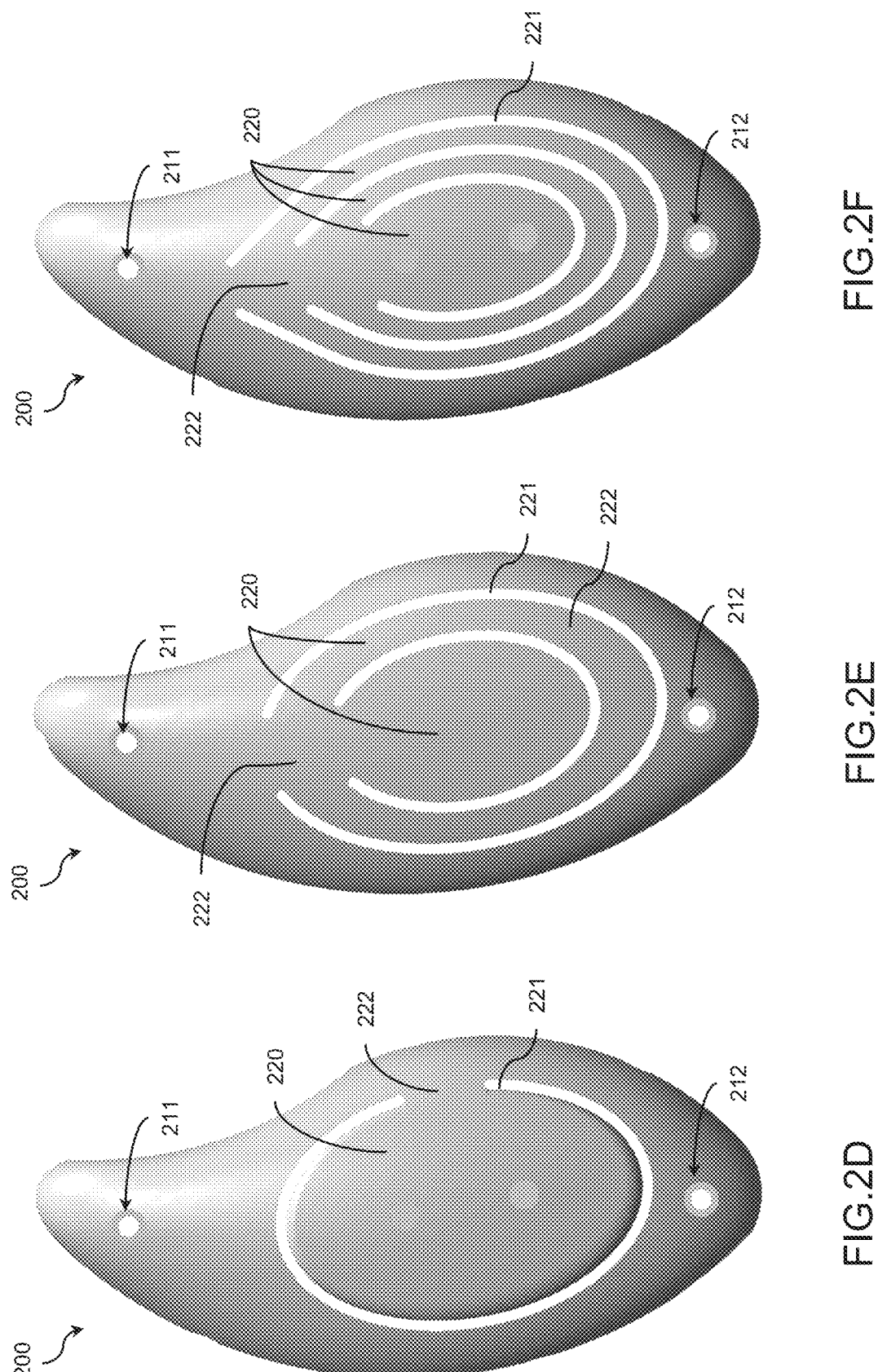
Figure 2H:
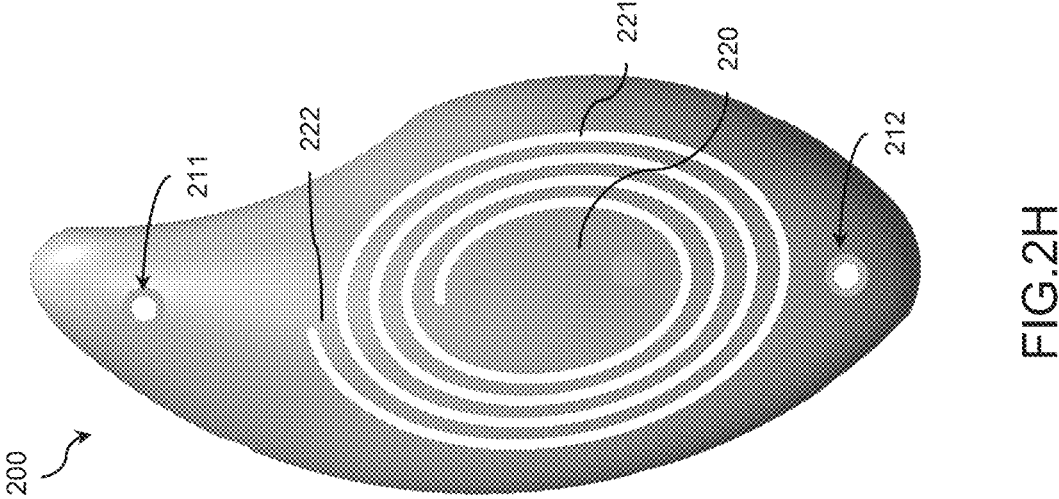
Figure 2G:
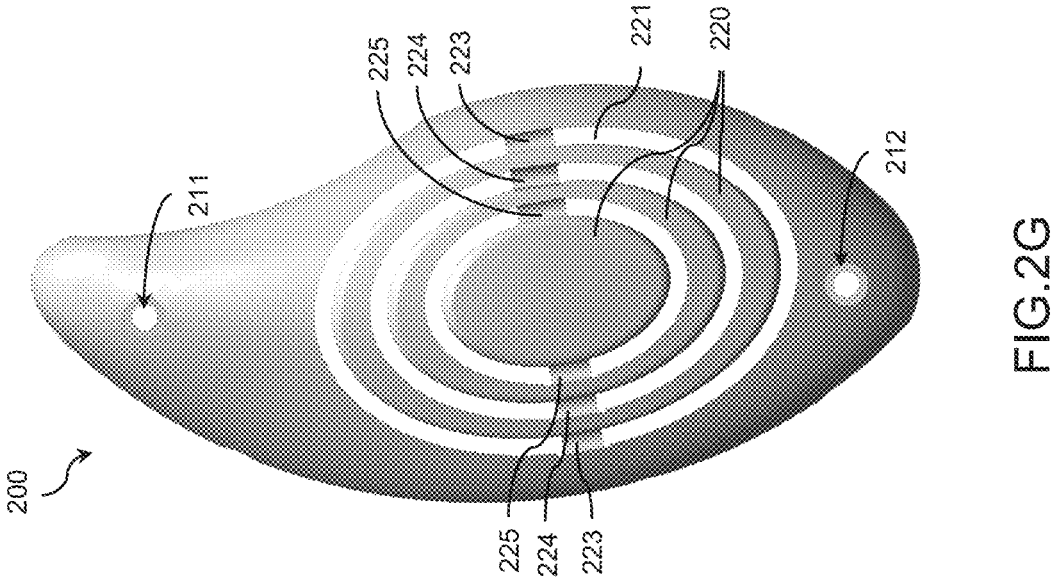

One or more slits 221 are provided in the outer casing 200. The slits are long narrow openings in the outer casing 200, as shown in FIG. 2. One or more portions 220 are thus obtained which may be displaced with respect to the remaining portion of the outer casing 200. The slits thus divide the outer casing into at least one portion 220 which may be displaced with respect to the remaining portion. These displaceable portions 220 may be connected to the remaining portion via one or more flexible portions 222. The flexible portions 222 form a hinge mechanism similar to a living hinge mechanism as detailed below. Alternatively, the portions 220 may be disconnected from the remaining portion of the outer casing. In this case, the displaceable portions 220 need to be connected to the remaining portion via for example flexure bearings 223, . . . , 225, i.e. thin "hinge" areas, as shown in FIG. 2G. The flexure bearings 223, . . . , 225 may be made from the same material as the outer casing or from a flexible material, such as an elastic or a rubber flat band. Instead of flexure bearings, a mechanical bearing may be used to connect the displaceable portions 220 with the remaining portion of the outer casing.

FIG. 2 shows various example designs of displaceable portions 220. FIG. 2A shows an outer casing 200 with a plurality of thin, narrow and arced slits 221 arranged in a concentric fashion. One displaceable portion 220 is formed which is connected to the remaining portion via the material remaining in between the slits. The remaining material which moves and flexes, forms a flexible portion 222. The flexible portion 222 allows the displaceable portion 220 to be displaced with respect to the remaining portion of the outer casing. The flexible portion 222 thus acts as a hinge similar to a living hinge. A true "living" hinge may as well be made, by thinning of the material along the line of the flexible portion. This may be beneficial when a higher range of flexing of the flexible portion is required. FIG. 2B and FIG. 2C show an outer casing 200 with elongated and organically shaped slits 221 arranged in a concentric fashion. Similarly, to the example of FIG. 2A, herein again the displaceable portion 220 is connected to the remaining portion of the outer casing 200 via a hinge 222. FIG. 2D, FIG. 2E and FIG. 2F show respectively one, two and three thin narrow elliptical slits 221. The thus formed one, two and three displaceable portions connect to the remaining portion of the outer casing 200 via a shared hinge 222. FIG. 2G shows three circular slits 221 forming three displaceable portions 220 separated from each other and from the remaining portion. The displaceable portions are connected to the remaining portion of the outer casing 200 via flexure bearings 223, 224 and 225. As shown in the figure, the inner most displaceable portion connects to the middle one via the flexure bearing 225, the middle one to the outer most displaceable portion via the flexure bearing 224, and, the outer most to the remaining portion of the outer casing via the flexure bearing 223. The flexure bearings 223, 224 and 225 are made of a narrow thing structure which may be made of the same material as the outer casing or another material, such as silicone, TPE or another flexible material. FIG. 2H shows a spiraling slit 221 forming one displaceable portion 220 and a spiral flexible portion 222.

Referring back to FIG. 1A, the drive unit 400 comprises a motor 410, a camshaft and, optionally, a cantilever 420. The motor 410 may be an electrical motor, such as a brushed or a brushless DC motor, solenoid, rotary solenoid, servo motor, etc. A brushless DC motor is also known as a stepper motor. The camshaft comprises a shaft 411 and a cam 412. One end of the shaft is connected to the motor 410 so that it is rotated by the motor, and, the other end is connected to the cam 412. The rotary movement of the camshaft is translated into a linear motion, for example up and down or back and forth motion in an object engaged with the cam, i.e. the follower.

The cam 412 may engage directly with the outer casing 200. The cam engages with the displaceable portion 220. The rim of the cam is in direct contact with the displaceable portion 220. Thus, when the camshaft rotates, the cam exerts a force onto the displaceable portion 220 causing the outer casing to expand or to contract. For example, when the cam pushes the displaceable portion 220 outwards, the flexible portion flexes 222 and the outer casing 200 expands. When the exerted force by the cam is lower than the force exerted by the flexible portion 222, the outer casing 200 contracts back to a normal state. The amount of displacement of the outer casing depends on the shape and dimensions of the cam 412 as well as on the position at which the cam is in contact with the displaceable portion.

Alternatively, the cam may engage with a plurality of displaceable portions 220. For example, the cam may be provided with a plurality of protrusions extending out and upwards of the rim of the cam, each engaging with a respective displaceable portion. For example, three protrusions would be required to displace the three displaceable portions 220 of FIG. 2F. Alternatively, instead of a single cam, multiple cams may be provided on the shaft. In this case, each cam will be designed such that it engages with a respective displaceable portion.

Alternatively, the cam may engage indirectly with the outer casing, for example, via a cantilever 420 as shown in FIG. 1A. In this case, the cam may engage with the one or more displaceable portions 220 via the cantilever 420. The cantilever 420 may be anchored at an anchor point 422 (as shown in the figure) around which it may rotate. One end of the cantilever 421, i.e. its first end, is arranged to be in contact with the outer casing 200. For example, the cantilever end 421 may be arranged to be in contact with or attached to the displaceable portions via an attach and detach mechanism 220. The attach and detach mechanism 220 may be for example. The cantilever end 421 may have an elongated shape so that the cantilever end 421 engages at multiple locations with the one or more displaceable portions along their surfaces. Additionally, the elongated cantilever end 421 may also be shaped such that it engages with the flexible portions 222 as well. This way both the displaceable portions and the flexible portions may be displaced. This allows to control how the shape of the outer casing changes. Furthermore, the cantilever end 421 may be curved. This allows to further control how the shape of the outer casing changes. For example, a gradual and smooth change of shape throughout the surface of the outer casing 200 may be achieved. The other end 423 of the cantilever 420, i.e. its second end, is arranged to be in contact with the cam 412. In this case, the amount of displacement of the outer casing depends on the shape and dimensions of the cam 412, the design of the cantilever, i.e. its shape and dimensions, as well as on the position at which the cantilever is in contact with the outer casing. By design of the cantilever, one should understand the distance between the respective cantilever ends 421 and 423 and the anchor point 422, the distance between the cantilever ends 421 and 423, as well as, the shape and dimensions of the cantilever end 421.

Figures 3, 4, 5:
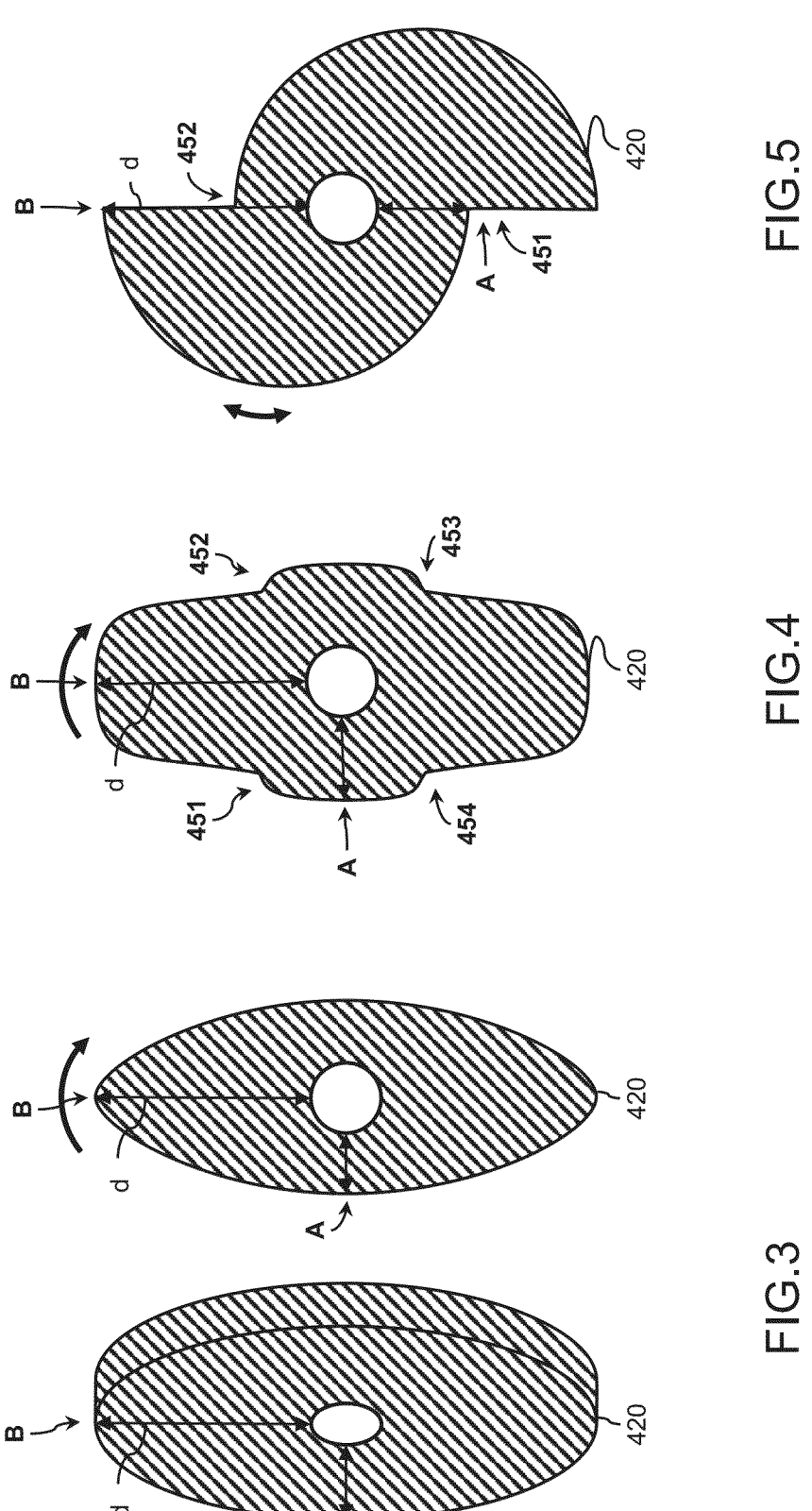
FIG. 3 shows an example embodiment of a cam according to the present disclosure.
FIG. 4 shows another example embodiment of a cam according to the present disclosure.
FIG. 5 shows yet another example embodiment of a cam according to the present disclosure.

The principle of operation of the device of FIG. 1A will be now explained with reference and FIG. 3. FIG. 3 shows an example of a cam 412 with an ellipsoid shape. When the cantilever end 423 is in contact with the cam at position 'A', i.e. when the distance d between the centre of rotation of the cam and the cantilever end 423 is lowest, the cantilever end 423 is at its lowest position while the other cantilever end 421 is at its highest position. There is pressure, or push, exerted by the cantilever end 421 onto the outer casing 200—the outer casing 200 is in a fully expanded state. As the camshaft rotates, the cam rotates from position 'A' to position 'B'. The distance between the centre of rotation of the cam and the cantilever end 421 gradually changes from lowest to highest. This causes the cantilever 420 to pivot around its anchor point 422. As a result, the cantilever end 423 gradually moves upwards to its highest position and the cantilever end 421 gradually moves downwards to its lowest position, as shown in FIG. 1A with the arrows. The cantilever end 421 thus pulls the displaceable portion inwards and causes the outer casing 200 to gradually contract from position 'AA' to position 'BB'. As a result, when the cantilever end 423 is in contact with the cam at position 'A', the outer casing 200 reaches a fully expanded state. The transition from a fully expanded state to a fully contracted state corresponds to a 'breathe out' phase, while the transition from a fully contracted state to a fully expanded state to a 'breathe in' phase.

One full rotation of the cam outputs two full breathing cycles, i.e. the outer casing will reach a fully expanded state and a fully contracted state twice. Depending on the speed of rotation of the camshaft, the length of the 'breathe in' and 'breathe out' phases may be controlled. In other words, the pace with which the outer casing expands, or, contracts, may be varied. Various breathing patterns may thus be provided by the respiration guidance device.

FIG. 4 shows another example of a cam 412 with a more complex shape which allow to stop the rotation of the motor and hence the cam to emulate a 'breathe hold' phase. As shown in the figure, the cam comprises four convex portions separated by four concave portions 451 to 454. Two of the convex portions are bigger than the other two. The rim of the cam is substantially flat between the concave portions 451 and 454, and between the concave portions 452 and 453. Similarly, the rim of the cam in the neighbourhood area around the position 'B' is also substantially flat. Within these flat areas the contraction or expansion of the outer casing is negligible and thus not perceived by the user. This allows emulating a breath hold phase between the 'breathe in' and 'breathe out' phases. Similarly to the cam of FIG. 3, when the cam rotates from position 'A' to position 'B' and so on as indicated by the arrow in the figure, one full rotation of the cam outputs two full breath cycles. Depending on the speed of rotation, the length of the 'breathe in', 'breathe out' and the 'breathe hold' phases may be varied.

Similar operation may be achieved with the cam shown in FIG. 5. In this case, however, the motor rotates in one direction, for example, from position 'A' to position 'B' and then in the opposite direction to emulate a 'breathe in' and 'breathe out' phases. 'Breathe hold' phase may be emulating by pausing the rotation of the motor when the motor rotation transitions from a clockwise to a counterclockwise and vice versa.

Figure 1B:
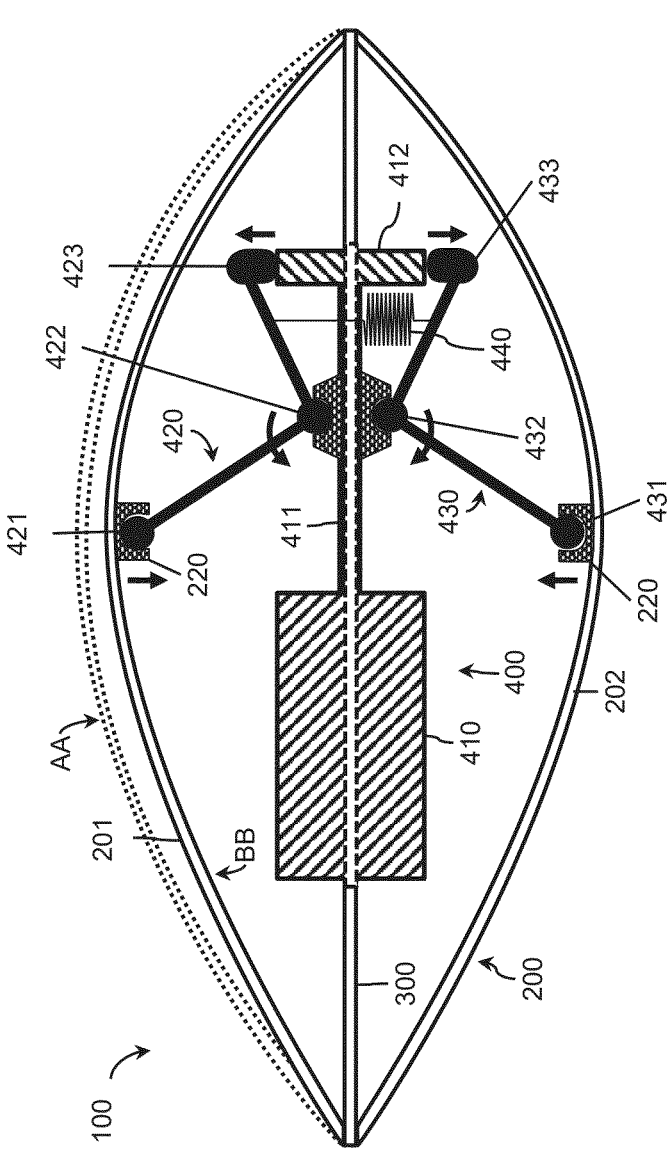
FIG. 1B shows another example embodiment of the respiration guidance device according to the present disclosure.

FIG. 1B shows another example embodiment of the respiration guidance device similar to the one shown in FIG. 1A. In this example embodiment, the outer casing 200 comprises two sections 201 and 202 separated by the platform 300 and the drive unit comprises, optionally, two cantilevers 420 and 430. Both sections comprise one or more slits 221 as shown in FIG. 2 forming one or more displaceable portions 220. The displaceable portions 220 may be connected to the remaining portion of the respective sections 201 and 202 via one or more flexible portions 222 forming a hinge mechanism similar to a living hinge, or, via flexure bearings 223, 224 and 225 as shown in FIG. 2G. The both sections 201 and 202 may be designed in the same or similar way, i.e. to have the same or similar tactile area and change of shape. Both sides of the outer casing 200 may thus expand and contract in the same or similar manner.

The cam may have same or similar shape and dimensions as discussed above with reference to FIG. 3, FIG. 4 and FIG. 5. The cam 412 may engage directly or indirectly with the respective sections 201 and 202 of the outer casing 200. In the former case, when the cam engages directly with the displaceable portions of both sections, the device will operate as detailed above with reference to FIG. 1A. In the latter case, the drive unit 400 is provided with two cantilevers 420 and 430 which are configured to displace the displaceable portions of the respective sections 201 and 202 with respect to their remaining portions. The cantilevers 420 and 430 may have the same design, i.e. same shape and dimension, which allows to obtain same range of expansion or contraction of the both sections. Alternatively, the cantilevers may have different design so that the range of expansion or contraction of the sections is different. The cantilevers 420 and 430 may be anchored at an anchor point 422 and 433, respectively. The first end 421 of cantilever 420 is arranged to be in contact with the one or more displaceable portions of section 201 and its other end 423 in contact with the cam 412. The first end 431 of cantilever 430 is arranged to be in contact with the one or more displaceable portions of section 202 and its other end 433 is arranged to be in contact with the cam 412. The cantilevers' end 423 and 433 are in contact with the cam 412 at opposite sides. Similarly to the embodiment of FIG. 1A, the cantilever ends 421 and 431 may be arranged to be in contact with or attached to the one or more displaceable portions via an attach and detach mechanism 220.

Depending on the design of the cantilevers' end 421 and 431, the cam 412 may exert a force onto the displaceable portions of the respective sections, and, optionally, to the flexible portions, as detailed above with reference to the embodiment of FIG. 1A.

To assure simultaneous expansion or contraction of sections 201 and 202, the cantilevers 420 and 430 are connected together via a spring 440. Such spring guarantees that the cantilever ends 423 and 433 remain in good contact with the cam 412 while the cam rotates. Spring 440 may be designed for compression and/or tension or may be designed as a torsion spring, etc.

If a compression spring is used connecting the cantilever ends 421 and 431 together, the respiration guidance device will operate as detailed above with reference to FIG. 1A and FIG. 3. A compression spring operates with a compression load. Such a compression spring forces the outer casing to be in a fully expanded. This state may be referred as a normal state as no compression load is applied to the spring. The spring forces the cantilevers 420 and 430 to pivot such that the cantilever ends 421 and 431 are at their highest position and cantilever ends 423 and 433 at their lowest position. That is, with the rotation of the cam, the outer casing 200 will be contracting from a fully expanded state to a fully contracted state and back.

The same operation may be achieved by using a tension spring connecting the cantilevers' end 423 and 433 together, as shown in FIG. 1B. The principle of operation of the device of FIG. 1B will be explained with reference to FIG. 3. When the cantilevers' end 423 and 433 are in contact with the cam 412 at position 'A', the cantilevers' end 423 and 433 are at their lowest position while the other cantilevers' end 421 and 431 are at their highest position. The spring 440 is thus in a contracted, or a normal state, i.e. the cam does not exert a tension load on the spring and the spring 440 is not stretched. The cantilevers' end 421 and 431 exert pressure, or push, onto the outer casing 200—the outer casing 200 is in an expanded, or normal, state. As the cam rotates from position 'A' to position 'B', the distance between the centre of rotation of the cam and the respective cantilevers' end 423 and 433 gradually changes from lowest to highest. This causes the cantilevers 420 and 430 to pivot around their respective anchor point 422 and 432. The cantilevers' end 423 and 433 thus move upwards to their highest position and the cantilevers' end 421 and 431 downwards to their lowest position, as shown in FIG. 1B with the arrows. The cantilevers' end 421 and 431 thus pull the displaceable portion inwards and cause the outer casing 200 to gradually contract from position 'AA' to position 'BB'. As a result, when the cantilevers' end 423 and 433 are in contact with the cam at position 'B', the outer casing 200 reaches a fully contracted state. As the tension load on the spring increases, the spring 440 tries to contract back to its normal state and thus forces the two cantilever ends 423 and 433 to remain in a good contact with the rim of the cam 412.

In case the cam engages directly with the displaceable portions of the respective sections, the amount of displacement of the outer casing depends on the shape and dimensions of the cam 412 as well as on the position at which the cam is in contact with the displaceable portions 220.

In case the cam engages with the outer casing via the cantilevers 420 and 430, the amount of displacement of the outer casing depends on the shape and dimensions of the cam 412, the shape and dimensions of the cantilevers 420 and 430 as well as on the position at which the cantilevers engage with the displaceable portions of the sections 201 and 202.

As detailed above, the range of displacement depends on the shape and dimensions of the cam and in case cantilevers are used, on the shape and dimensions of the cantilevers as well as on the position at which the cantilevers engage with the displaceable portions. A displacement in the range of 1 mm up to 20 mm may be provided by the implementations described with reference to FIGS. 1A and 1B. Displacement range between 1 mm up to 4 mm may provide a reliable tactile signal for users with smaller hands and/or when the device is held in one hand. However, this displacement range may not be sufficient to provide a reliable tactile signal if the device is held with two hands. Displacement range between 4 mm up to 10 mm may be considered providing a reliable tactile signal while providing comfortable user experience irrespective whether the user holds the device in one hand or with both hands. A displacement range above 10 mm and up to 20 mm offers a reliable tactile signal when the device is held with both hands. However, it may not be comfortable for the user, especially for users with smaller hands, if the device is held in one hand.

Although in the present disclosure the drive unit is used to change the shape of an outer casing made of rigid or semi-rigid material as described with reference to FIG. 1A and FIG. 1B, it should be appreciated that the drive unit may as well be used to modify the shape of an outer casing made of flexible material, such as silicon, gel-like material, foam materials, such as thermoplastic polyurethane, TPU, foam or other suitable flexible materials.

Figure 6:
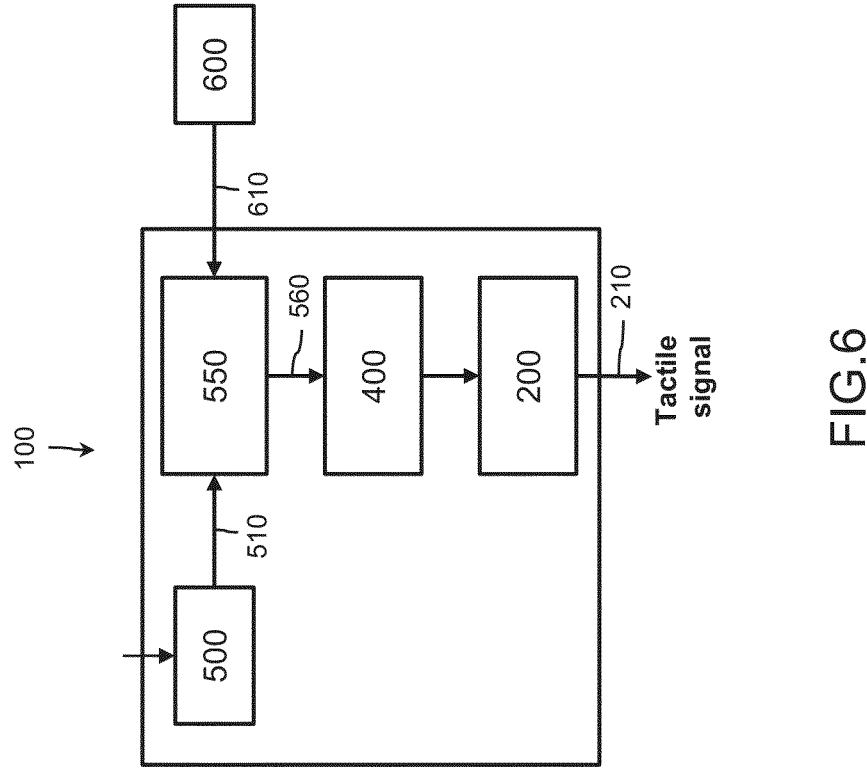
FIG. 6 shows an example embodiment of a block diagram of the respiration guidance device according to the present disclosure.

FIG. 6 shows an example of a block diagram of the respiration guidance device according to the present disclosure. The respiration guidance device comprises a sensor unit 500, a control unit 550, a drive unit 400, a tactile output unit (i.e. the outer casing) 200, and, optionally, a memory unit.

The memory unit (not shown in the figure) may be a volatile memory, a non-volatile memory or a combination thereof. The memory unit may store program instructions, breathing patterns and any other data needed by the control unit 550 for controlling the operation of the drive unit 400 and therefore the breathing pattern.

The sensor unit 500 may comprise one or more sensors configured to measure a physiological characteristic of the person—the user of the device. For example, the sensor unit 500 may comprise a hear rate sensor which generates an electrical signal 510 indicative of a heart rate of a person. Based on the electrical signal 510 the control unit determines a desired breathing pattern 560 according to which the speed of rotation of the motor 410 of the drive unit 400 is controlled. The thus determined desired breathing pattern defines how the outer casing 200 of the respiration guidance device 100 changes shape, i.e. how fast the transition from a fully expanded to a fully contracted state will be performed and possibly how long is the duration of the 'breathe hold' phase. The outer casing 200 thus outputs the tactile signal 210.

The determined desired breathing pattern may be transmitted wirelessly to an external device 600, such as a smart watch, a smart phone, laptop or a similar device. The person may thus modify the determined breathing pattern by for example changing the length of the 'breathe in' and/or the length of the 'breathe out' phase. Further, it may add a 'breathe hold' phase between the 'breathe in' and/or 'breathe out' phases. The modifications to the breathing pattern may then be communicated to the respiration guidance device. Alternatively, the respiration device 100 may be configured to connected to the external device 600 via a wired connection.

Further, different pre-determined breathing patterns may be stored on the external device 600. The user thus may select a pre-determined breathing pattern and upload the selected breathing pattern to the respiration device 100. The selected breathing pattern is transmitted (wirelessly or via a wired connection) to the control unit 550 and stored in the memory unit. The control unit 550 thus controls the drive unit in accordance with the selected breathing pattern. Similarly to above, modifications to the selected breathing pattern may be made by the user. The external device 600 thus communicates the modifications of the breathing pattern to the control unit 550 as soon as they are made.

Alternatively, the processing of the electrical signal 510 generated by the sensor unit 500 and the determination of the desired breathing pattern 560 may be performed by the external device 600. In this case, the electrical signal 510 is transmitted to the external device 600 which determined the desired breathing pattern based on the electrical signal. Thus, all the processing complexity is migrated to the external device.

To lighten the processing complexity on the external device 600, the processing may be done on the cloud. In that case, upon reception of the electrical signal 510 from the device 100, the external device 600 will forward the latter to the cloud. The desired breathing pattern will be determined on the cloud and send back to the external device 600. Upon reception of the desired breathing pattern from the cloud, the external device 600 will transmit it to the respiration guidance device as detailed above.

Although the present invention has been illustrated by reference to specific embodiments, it will be apparent to those skilled in the art that the invention is not limited to the details of the foregoing illustrative embodiments, and that the present invention may be embodied with various changes and modifications without departing from the scope thereof. The present embodiments are therefore to be considered in all respects as illustrative and not restrictive, the scope of the invention being indicated by the appended claims rather than by the foregoing description, and all changes which come within the scope of the claims are therefore intended to be embraced therein.

It will furthermore be understood by the reader of this patent application that the words "comprising" or "comprise" do not exclude other elements or steps, that the words "a" or "an" do not exclude a plurality, and that a single element, such as a computer system, a processor, or another integrated unit may fulfil the functions of several means recited in the claims. Any reference signs in the claims shall not be construed as limiting the respective claims concerned. The terms "first", "second", third", "a", "b", "c", and the like, when used in the description or in the claims are introduced to distinguish between similar elements or steps and are not necessarily describing a sequential or chronological order. Similarly, the terms "top", "bottom", "over", "under", and the like are introduced for descriptive purposes and not necessarily to denote relative positions. It is to be understood that the terms so used are interchangeable under appropriate circumstances and embodiments of the invention are capable of operating according to the present invention in other sequences, or in orientations different from the one(s) described or illustrated above.

The invention claimed is:

1. A respiration guidance device comprising:
an outer casing configured to change shape; and
a drive unit located within the outer casing and configured to change the shape of the outer casing according to a desired breathing pattern; and
wherein the outer casing comprises at least one slit dividing the outer casing into at least one portion displaceable with respect to a remaining portion of the outer casing; and
wherein the drive unit is configured to change the shape of the outer casing by displacing the at least one portion;
wherein the drive unit comprises a camshaft for translating a rotational movement into the displacement of the outer casing;
wherein the drive unit further comprises at least one cantilever for transforming the movement of the camshaft into the displacement of the outer casing;

wherein the at least one cantilever is configured to engage with the at least one portion at one end and to engage with the camshaft at the other end; and wherein the at least one cantilever is configured to disengage from the at least one portion upon exerting an external pressure on the outer casing.

2. The respiration guidance device according to claim 1, wherein the at least one portion comprises at least one flexible portion configured to connect the at least one portion with the remaining portion.

3. The respiration guidance device according to claim 1, wherein the outer casing is configured to expand or contract upon displacing the at least one portion with respect to the remaining portion.

4. The respiration guidance device according to claim 1, wherein the outer casing comprises a first section and a second section configured to be fastened together, each section comprising at least one slit dividing the respective section into at least one portion displaceable with respect to a remaining portion of the respective section, and, wherein the drive unit is configured to change the shape of the respective sections by displacing their respective the at least one portion.

5. The respiration guidance device according to claim 4, wherein the first section and the second section are configured to expand or contract simultaneously upon displacing the respective at least one portions.

6. The respiration guidance device according to claim 1, wherein the at least one cantilever is configured to engage with the at least one portion at multiple locations.

7. The respiration guidance device according to claim 1, further comprising at least one sensor configured to generate an electrical signal indicative of a physiological characteristic of a person, and, a control unit configured to determine the desired breathing pattern based on the generated electrical signal and to operate the drive unit in accordance with the desired breathing pattern.

8. The respiration guidance device according to claim 7, wherein the at least one sensor comprises a heart rate sensor for generating an electrical signal indicative of a heart rate of the person.

9. The respiration guidance device according to claim 1, wherein the outer casing is covered by or enclosed within a flexible material.

10. The respiration guidance device according to claim 1, wherein the device is hand-held.

* * * * *